US006277574B1

(12) United States Patent
Walker et al.

(10) Patent No.: US 6,277,574 B1
(45) Date of Patent: Aug. 21, 2001

(54) GENES ASSOCIATED WITH DISEASES OF THE KIDNEY

(75) Inventors: Michael G. Walker, Sunnyvale; Wayne Volkmuth, Menlo Park; Tod M. Klingler, San Carlos; Yalda Azimzai, Hayward; Henry Yue, Sunnyvale, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/289,349

(22) Filed: Apr. 9, 1999

(51) Int. Cl.$^7$ .............................. C12Q 1/68; C12N 15/63; C07H 21/04
(52) U.S. Cl. ........................ 435/6; 435/252.3; 435/320.1; 435/325; 536/23.1; 536/24.3; 536/24.31; 536/24.33
(58) Field of Search ................................. 536/23.1, 23.2, 536/24.31, 24.3, 24.33; 435/320.1, 69.1, 6, 375, 325, 257.3; 514/44

(56) References Cited

U.S. PATENT DOCUMENTS 5,747,256 * 5/1998 Yan et al. ................................ 435/6

FOREIGN PATENT DOCUMENTS

WO 98/32853 * 7/1998 (WO).

OTHER PUBLICATIONS

Stuart H. Orkin, Report and Recommendations of the Panel to Assess the NIH Investment in Research on Gene Therapy, pp. 1–25, Dec. 1995.*
Verma et al. Gene therapy–promises, problems and prospects., Nature, vol. 389, pp. 239–242, Sep. 1997.*
W. French Anderson, Human gene therapy, Nature, vol. 392, Supp., pp. 25–30, Apr. 1998.*
Andrea D. Branch, A good antisense molecule is hard to find, TIBS, 47–48, Feb. 1998.*
Trisha Gura, Antisense Has Growing Pains, Science, pp. 575–577, Oct. 1995.*
Stanley Crooke, Antisense '97: A roundtable on the state of the industry, Nature Biotechnology, p. 522, Jun. 1997.*
Stanley Crooke, Antisense Research and Applications, Chapter 1, Basic Principles of Antisense Therapeutics, Springer–Verlag Press, Berlin, Heidelberg, New York, p. 3, Jul. 1998.*
Aicher, L., et al., Abstract, New insights into cyclosporine A nephrotoxicity by proteome analysis, *Electrophoresis*, 19(11):1998–2003, (1998).
Ali, M., et al., Abstract, Hereditary fructose intolerance, *J Med Genet*, 35 (5):353–65, (1998).
Ali, M., et al., Abstract, DNA diagnosis of fatal fructose intolerance from archival tissue, *Q J Med*, 86(1):25–30, (1993).

Derst, C., et al., Abstract, Mutations in the ROMK gene in antenatal Barter syndrome are associated with impaired K+ channel function, *Biochem Biophys Res Commun*, 230 (3):641–5, (1997).
Hallson, PC, et al., Abstract, Effects of Tamm–Horsfall protein with normal and reduced sialic acid content upon the crystallization of calcium phosphate and calcium oxalate in human urine, *Br J Urol*, 80(4):533–8, (1997).
Jones, DH, et al., Abstract, Embryonic expression of the putative gamma subunit of the sodium pump is required for acquisition of fluid transport capacity during mouse blastocyst development, *J Cell Biol*, 139 (6):1545–52, (1997).
Kamijo, T., et al., Abstract, Renal abnormality of calcium handling in spontaneously hypertensive rats, *Kidney Int Suppl*, 55:S166–8, (1996).
Kim, JW, et al., Abstract, Cloning and expression of human cDNA encoding Na+, K(+)–ATPase gamma–subunit, *Biochim Biophys Acta*, 1350 (2):133–5, (1997).
Kocher, O., et al., Abstract, Identification and partial characterization of PDZK1: a novel protein containing PDZ interaction domains, *Lab Invest*, 78(1):117–25, (1998).
MacLean, FR, et al., Abstract, Acute changes in urine protein excretion may predict chronic ifosfamide nephrotoxicity: a preliminary observation, *Cancer Chemother Pharmacol*, 41(5):413–6, (1998).
Mastroianni, N., et al., Abstract, Novel molecular variants of the Na–Cl contransporter gene are responsible fo Gitelman syndrome, *Am J Hum Genet*, 59(5):1019–26, (1996).
Miyamoto, K., et al., Abstract, Cloning and functional expression of a Na(+)–dependent phosphate co–transporter from human kidney cDNA cloning and functional expression, *Biochem J*, 305 (Pt 1):81–5, (1995).
Miyamoto, K., et al., Abstract, Chromosome assignments of genes for human Na(+)–dependent phosphate co–transporters NaPi–3 and NPT–1, *Tokushima J Exp Med*, 42(1–2):5–9, (1995).
Rodriguez–Soriano, J., Abstract, Bartter and related syndromes: the puzzle is almost solved, *Pediatr Nephrol*, 12(4):315–27, (1998).
Sharma, JN, et al., Abstract, Blood pressure regulation by the kallikreinkinin system, *Gen Pharmacol*, 27(1):55–63, (1996).
Simon, DB, et al., Abstract, Bartter's syndrome, hypokalaemic alkalosis with hypercalciuria, is caused by mutations in the Na–K–2Cl cotransporter NKCC2, *Nat Genet*, 13(2):183–8, (1996).

(List continued on next page.)

*Primary Examiner*—John L. LeGuyader
*Assistant Examiner*—Janet Epps
(74) *Attorney, Agent, or Firm*—Incyte Genomics, Inc.; Lynn E. Murry, PhD

(57) ABSTRACT

The invention provides novel kidney disease-associated genes and polypeptides encoded by those genes. The invention also provides expression vectors, host cells, and antibodies. The invention also provides methods for diagnosing, treating or preventing diseases of the kidney.

4 Claims, No Drawings

OTHER PUBLICATIONS

Sullivan, LP, et al., Abstract, Epithelial transport in polycystic kidney disease, *Physiol Rev*, 78(4):1165–91, (1998).

Tokuc, G., et al., Abstract, Renal dysfunctions secondary to ifosfamide treatment in children, *J Exp Clin Cancer Res*, 16(2):227–30, (1997).

Torfvit, O., et al., Abstract, Urinary excretion of Tamm–Horsfall protein and epidermal growth factor in chronic nephropathy, *Nephron*, 79(2):167–72, (1998).

Yano, H., et al., Abstract, Alternative splicing of human inwardly rectifying K+ channel ROMK1 mRNA, *Mol Pharmacol*, 45(5):854–60, (1994).

Hilgers, K.F., et al., (Direct Submission), GenBank Sequence Database (Accession AFO6238), National Center for Biotechnology Information, National Library of Medicine, Bethesda, Maryland, 20894 (GI 3127192).

Hilgers, K.F., et al., (Direct Submission), GenBank Sequence Database (Accession AAD05209), National Center for Biotechnology Information, National Library of Medicine, Bethesda, Maryland, 20894 (GI 3127193).

Morrison, B.W., et al., (Direct Submission), GenBank Sequence Database (Accession X93036 S74645), National Center for Biotechnology Information, National Library of Medicine, Bethesda, Maryland, 20894 (GI 1085025).

Morrison, B.W., et al., (Direct Submission), GenBank Sequence Database (Accession CAA63606), National Center for Biotechnology Information, National Library of Medicine, Bethesda, Maryland, 20894 (GI 1085068).

\* cited by examiner

GENES ASSOCIATED WITH DISEASES OF THE KIDNEY

FIELD OF THE INVENTION

The invention relates to nine genes associated with diseases of the kidney as identified by their coexpression with genes known to be associated with renal disorders. The invention also relates to polypeptides encoded by these genes and to the use of these amino acid and nucleic acid sequences in the diagnosis, prognosis, prevention, treatment, and evaluation of therapies for diseases of the kidney.

BACKGROUND OF THE INVENTION

The kidneys excrete waste and contribute to maintenance of homeostasis by regulating blood pH, electrolyte levels and blood pressure. Renal failure or dysfunction is the cause of several diseases whose clinical manifestations are typically hyper- or hypo-tension. These diseases include Bartter's syndrome, Gitelman syndrome, autosomal dominant polycystic kidney disease, and nephrolithiasis.

Treatment with antibiotics such as gentamicin, tobramycin, or amikacin can lead to tubular necrosis with consequent risk of acute renal failure in as much as 25% of patients. A cumulative dose of 2 to 3 grams amphotericin B is likewise nephrotoxic. Cyclosporine, an immunosuppressant given to organ transplant patients, is also nephrotoxic. The molecular basis for the nephrotoxicity of these and other compounds is not understood, although calbindin D levels appear to be a useful diagnostic marker signaling cyclosporine-induced nephrotoxicity (Aicher et al. (1998) Electrophoresis 19:1998–2003). Similarly, reductions in urinary excretion of proteins such as Tamm-Horsfall protein, beta 2 microglobin, and urinary retinol binding protein, appear to be diagnostic for nephrctoxicity when induced by certain chemotherapeutic agents including ifosfamide and cisplatinum (MacLean et al. (1998) Cancer Chemother. Pharmacol. 41:413–6; Tokuc et al. (1997) J. Exp. Clin. Cancer Res. 16:227–30).

We have identified nine novel kidney disease-associated genes through their co-expression with genes known to affect kidney function in normal and diseased states. The present invention satisfies a need in the art by providing new amino acid and nucleic acid compositions that are useful for diagnosis, prognosis, treatment, prevention, and evaluation of therapies for renal disorders.

SUMMARY OF THE INVENTION

In one aspect, the invention provides for a substantially purified polynucleotide comprising a gene that is coexpressed with one or more known kidney disease-associated genes in a plurality of biological samples. Preferably, known kidney disease-associated genes are selected from the group consisting of uromodulin, NKCC2 (bumetanide-sensitive Na—K—Cl cotransporter 2), NCCT (thiazine-sensitive Na—Cl cotransporter), aldolase B, ROMK1 (inwardly-rectifying voltage-gated K channel), ATP1G1 (Na—K ATPase gamma subunit), PDZK1 (PDZ domain-containing protein), NPT-1 (Na-dependent phosphate cotransporter), calbindin, kininogen, and CIC-Kb (chloride channel). Preferred embodiments include (a) a polynucleotide sequence selected from the group consisting of SEQ ID NO:1, SEQ ID NO:2, SEQ ID NO:3, SEQ ID NO:4, SEQ ID NO:5, SEQ ID NO:7, SEQ ID NO:8, and SEQ ID NO:9 (SEQ ID NO: 1–5and 7–9); (b) a polynucleotide sequence which encodes a polypeptide sequence selected from the group consisting of SEQ ID NO:10, SEQ ID NO:11, and SEQ ID NO:12 (SEQ ID NO:10–12); (c) a polynucleotide sequence having at least 75% identity to the polynucleotide sequence of (a) or (b); (d) a polynucleotide sequence which is complementary to the polynucleotide sequence of (a), (b), or (c); (e) a polynucleotide sequence comprising at least 10, preferably at least 18, sequential nucleotides of the polynucleotide sequence of (a), (b), (c), or (d); or (f) a polynucleotide which hybridizes under stringent conditions to the polynucleotide of (a), (b), (c), (d), or (e). Furthermore, the invention provides an expression vector comprising any of the above described polynucleotides, and a host cell containing the expression vector. Still further, the invention provides a method for treating or preventing a disease or condition associated with the altered expression of a gene that is coexpressed with one or more known kidney disease-associated genes comprising administering to a subject in need a polynucleotide described above in an amount effective for treating or preventing the disease.

In a second aspect, the invention provides a substantially purified polypeptide comprising the gene product of a gene that is coexpressed with one or more known kidney disease-associated genes in a plurality of biological samples. The known kidney disease-associated gene may be selected from the group consisting of uromodulin, NKCC2, NCCT, aldolase B, ROMK1, ATP1G1, PDZK1, NPT-1, calbindin, kininogen, and CIC-Kb. Preferred embodiments are (a) the polypeptide sequence selected from the group consisting of SEQ ID NO:10–12; (b) a polypeptide sequence having at least 85% identity to the polypeptide sequence of (a); and (c) a polypeptide sequence comprising at least 6 sequential amino acids of the polypeptide sequence of (a) or (b). Additionally, the invention provides antibodies that bind specifically to any of the above described polypeptides and a method for treating or preventing a disease or condition associated with the altered expression of a gene that is coexpressed with one or more known kidney disease-associated genes comprising administering to a subject in need such an antibody in an amount effective for treating or preventing the disease.

In another aspect, the invention provides a pharmaceutical composition comprising the polynucleotide of claim 2 or the polypeptide of claim 3 in conjunction with a suitable pharmaceutical carrier and a method for treating or preventing a disease or condition associated with the altered expression of a gene that is coexpressed with one or more known kidney disease-associated genes comprising administering to a subject in need such a composition in an amount effective for treating or preventing the disease.

In a further aspect, the invention provides a method for diagnosing a disease or condition associated with the altered expression of a gene that is coexpressed with one or more known kidney disease-associated genes, wherein each known kidney disease-associated gene is selected from the group consisting of uromodulin, NKCC2, NCCT, aldolase B, ROMK1, ATP1G1, PDZK1, NPT-1, calbindin, kininogen, and CIC-Kb. The method comprises the steps of (a) providing a sample comprising one or more of the coexpressed genes; (b) hybridizing the polynucleotide of claim 2 to the coexpressed genes under conditions effective to form one or more hybridization complexes; (c) detecting the hybridization complexes; and (d) comparing the levels of the hybridization complexes with the level of hybridization complexes in a nondiseased sample, wherein altered levels of one or more of the hybridization complexes in a diseased sample compared with the level of hybridization complexes in a non-diseased sample correlates with the presence of the disease or condition.

Additionally, the invention provides antibodies, antibody fragments, and immunoconjugates that exhibit specificity to any of the above described polypeptides and methods for treating or preventing diseases or conditions of the kidney.

BRIEF DESCRIPTION OF THE SEQUENCE LISTING

The Sequence Listing provides exemplary kidney disease-associated gene sequences including polynucleotide sequences, SEQ ID NO:1–9, and the polypeptide sequences, SEQ ID NO:10–12. Each sequence is identified by a sequence identification number (SEQ ID NO) and by the Incyte clone number with which the sequence was first identified.

DESCRIPTION OF THE INVENTION

It must be noted that as used herein and in the appended claims, the singular forms "a", "an", and "the" include the plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Definitions

"NSEQ" refers generally to a polynucleotide sequence of the present invention, including SEQ ID NO:1–9. "PSEQ" refers generally to a polypeptide sequence of the present invention, SEQ ID NO:10–12.

A "fragment" refers to a nucleic acid sequence that is preferably at least 20 nucleic acids in length, more preferably 40 nucleic acids, and most preferably 60 nucleic acids in length, and encompasses, for example, fragments consisting of nucleic acids 1–50, 51–400, 401–4000, 4001–12,000, and the like, of SEQ ID NO:1–9.

"Gene" refers to the partial or complete coding sequence of a gene and to its 5' or 3' untranslated regions. The gene may be in a sense or antisense (complementary) orientation.

"Kidney disease-associated gene" refers to a gene whose expression pattern is similar to that of known kidney disease-associated genes which are useful in the diagnosis, treatment, prognosis, or prevention of diseases of the kidney. "Known kidney disease-associated gene" refers to a sequence which has been previously identified as useful in the diagnosis, treatment, prognosis, or prevention of diseases of the kidney. Typically, this means that the known gene is expressed at higher levels (i.e., has more abundant transcripts) in diseased or cancerous kidney tissue than in normal or non-diseased kidney or in any other tissue.

"Polynucleotide" refers to a nucleic acid, nucleic acid sequence, oligonucleotide, nucleotide, or any fragment thereof. It may be DNA or RNA of genomic or synthetic origin, double-stranded or single-stranded, and combined with carbohydrate, lipids, protein or other materials to perform a particular activity or form a useful composition. "Oligonucleotide" is substantially equivalent to the terms amplimer, primer, oligomer, element, and probe.

"Polypeptide" refers to an amino acid, amino acid sequence, oligopeptide, peptide, or protein or portions thereof whether naturally occurring or synthetic.

A "portion" refers to peptide sequence which is preferably at least 5 to about 15 amino acids in length, most preferably at least 10 amino acids long, and which retains some biological or immunological activity of, for example, a portion of SEQ ID NO:10–12.

"Sample" is used in its broadest sense. A sample containing nucleic acids may comprise a bodily fluid; an extract from a cell, chromosome, organelle, or membrane isolated from a cell; genomic DNA, RNA, or cDNA in solution or bound to a substrate; a cell; a tissue; a tissue print; and the like.

"Substantially purified" refers to a nucleic acid or an amino acid sequence that is removed from its natural environment and that is isolated or separated, and is at leasi: about 60% free, preferably about 75% free, and most preferably about 90% free, from other components with which it is naturally present.

"Substrate" refers to any suitable rigid or semi-rigid support to which polynucleotides or polypeptides are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

A "variant" refers to a polynucleotide or polypeptide whose sequence diverges from SEQ ID NO:1–9. Polynucleotide sequence divergence may result from mutational changes such as deletions, additions, and substitutions of one or more nucleotides; it may also be introduced to accommodate differences in codon usage. Each of these types of changes may occur alone, or in combination, one or more times in a given sequence.

The Invention

The present invention encompasses a method for identifying biomolecules that are associated with a specific disease, regulatory pathway, subcellular compartment. cell type, tissue type, or species. In particular, the method identifies genes useful in diagnosis, prognosis, treatment, prevention, and evaluation of therapies for diseases of the kidney including, but not limited, Bartter's syndrome, Gitelman syndrome, nephrolithiasis, renal amyloidosis, hypertension; primary aldosteronism; Addison's disease; renal failure; glomerulonephritis; chronic glomerulonephritis: tubulointerstitial nephritis; cystic disorders of the kidney and dysplastic malformations such as polycystic disease, renal dysplasias, and cortical or medullary cysts; inherited polycystic renal diseases (PRD), such as recessive and autosomal dominant PRD; medullary cystic disease; medullary sponge kidney and tubular dysplasia; Alport's syndrome; non-renal cancers which affect renal physiology, such as bronchogenic tumors of the lungs or tumors of the basal region of the brain; multiple myeloma; adenocarcinomas of the kidney; metastatic renal carcinoma; in addition, nephrotoxic disorders include any functional or morphologic change in the kidney produced by any pharmaceutical, chemical, or biological agent that is ingested, injected, inhaled, or absorbed. Some broad categories of common nephrotoxic agents are heavy metals, all classes of antibiotics, analgesics, solvents, oxalosis-inducing agents, anticancer drugs, herbicides and pesticides, botanicals and biologicals, and antiepileptics.

The method entails first identifying polynucleotides that are expressed in a plurality of cDNA libraries. The identified polynucleotides include genes of known or unknown function which are expressed in a specific disease process, subcellular compartment, cell type, tissue type, or species. The expression patterns of the genes with known function are compared with those of genes with unknown function to determine whether a specified coexpression probability threshold is met. Through this comparison, a subset of the polynucleotides having a high coexpression probability with the known genes can be identified. The high coexpression probability correlates with a particular coexpression probability threshold which is preferably less than 0.001 and more preferably less than 0.00001.

The polynucleotides originate from cDNA libraries derived from a variety of sources including, but not limited to, eukaryotes such as human, mouse, rat, dog, monkey, plant, and yeast; prokaryotes such as bacteria; and viruses. These polynucleotides can also be selected :From a variety of sequence types including, but not limited to, expressed sequence tags (ESTs), assembled polynucleotide sequences, full length gene coding regions, promoters, introns, enhancers, 5' untranslated regions, and 3' untranslated regions. To have statistically significant analytical results, the polynucleotides need to be expressed in at least three cDNA libraries.

The cDNA libraries used in the coexpression analysis of the present invention can be obtained from adrenal gland, biliary tract, bladder, blood cells, blood vessels, bone marrow, brain, bronchus, cartilage, chromaffin system, colon, connective tissue, cultured cells, embryonic stem cells, endocrine glands, epithelium, esophagus, fetus, ganglia, heart, hypothalamus, immune system, intestine, islets of Langerhans, kidney, larynx, liver, lung, lymph, muscles, neurons, ovary, pancreas, penis, peripheral nervous system, phagocytes, pituitary, placenta, pleurus, prostate, salivary glands, seminal vesicles, skeleton, spleen, stomach, testis, thymus, tongue, ureter, uterus, and the like. The number of cDNA libraries selected can range from as few as 3 to greater than 10,000. Preferably, the number of the cDNA libraries is greater than 500.

In a preferred embodiment, genes are assembled from related sequences, such as assembled sequence fragments derived from a single transcript. Assembly of the polynucleotide sequences can be performed using sequences of various types including, but not limited to, ESTs, extensions, or shotgun sequences. In a most preferred embodiment, the polynucleotide sequences are derived from human sequences that have been assembled using the algorithm disclosed in "Database and System for Storing, Comparing and Displaying Related Biomolecular Sequence Information", Lincoln et al. Ser. No:60/079,469, filed Mar. 26, 1998, incorporated herein by reference.

Experimentally, differential expression of the polynucleotides can be evaluated by methods including, but not limited to, differential display by spatial immobilization or by gel electrophoresis, genome mismatch scanning, representational difference analysis, and transcript imaging. Additionally, differential expression can be assessed by microarray technology. These methods may be used alone or in combination.

Known kidney disease-associated genes can be selected based on the use of these genes as diagnostic or prognostic markers or as therapeutic targets. Preferably. the known kidney disease-associated genes include uromodulin, NKCC2, NCCT, aldolase B, ROMK1, ATP1G1, PDZK1, NPT-1, calbindin, kininogen, and CIC-Kb, and the like.

The procedure for identifying novel genes that exhibit a statistically significant coexpression pattern with known kidney disease-associated genes is as follows. First, the presence or absence of a gene in a cDNA library is defined: a gene is present in a cDNA library when at least one cDNA fragment corresponding to that gene is detected in a cDNA sample taken from the library, and a gene is absent from a library when no corresponding cDNA fragment is detected in the sample.

Second, the significance of gene coexpression is evaluated using a probability method to measure a due-to-chance probability of the coexpression. The probability method can be the Fisher exact test, the chi-squared test, or the kappa test. These tests and examples of their applications are well known in the art and can be found in standard statistics texts (Agresti (1990) *Categorical Data Analysis*, John Wiley & Sons, New York N.Y.; Rice (1988) *Mathematical Statistics and Data Anaiysis*, Duxbury Press, Pacific Grove Calif.). A Bonferroni correction (Rice, supra, p. 384) can also be applied in combination with one of the probability methods for correcting statistical results of one gene versus multiple other genes. In a preferred embodiment, the due-to-chance probability is measured by a Fisher exact test, and the threshold of the due-to-chance probability is set preferably to less than 0.001, more preferably to less than 0.00001.

To determine whether two genes, A and B, have similar coexpression patterns, occurrence data vectors can be generated as illustrated in Table 1. The presence of a gene occurring at least once in a library is indicated by a one, and its absence from the library, by a zero.

TABLE 1

Occurrence data for genes A and B

| | Library 1 | Library 2 | Library 3 | ... | Library N |
|---|---|---|---|---|---|
| gene A | 1 | 1 | 0 | ... | 0 |
| gene B | 1 | 0 | 1 | ... | 0 |

For a given pair of genes, the occurrence data in Table 1 can be sumniarized in a 2×2 contingency table.

TABLE 2

Contingency table for co-occurrences of genes A and B

| | Gene A present | Gene A absent | Total |
|---|---|---|---|
| Gene B present | 8 | 2 | 10 |
| Gene B absent | 2 | 18 | 20 |
| Total | 10 | 20 | 30 |

Table 2 presents co-occurrence data for gene A and gene B in a total of 30 libraries. Both gene A and gene B occur 10 times in the libraries. Table 2 summarizes and presents: 1) the number of times gene A and B are both present in a library; 2) the number of times gene A and B are both absent in a library; 3) the number of times gene A is present, and gene B is absent; and 4) the number of times gene B is present, and gene A is absent. The upper left entry is the number of times the two genes co-occur in a library, and the middle right entry is the number of times neither gene occurs in a library. The off diagonal entries are the number of times one gene occurs, and the other does not. Both A and B are present eight times and absent 18 times. Gene A is present, and gene B is absent, two times; and gene B is present, and gene A is absent, two times. The probability ("p-value") that the above association occurs due to chance as calculated using a Fisher exact test is 0.0003. Assoc iations are generally considered significant if a p-value is less than 0.01 (Agresti, supra; Rice, supra).

This method of estimating the probability for coexpression of two genes makes several assumptions. The method assumes that the libraries are independent and are identically sampled. However, in practical situations, the selected cDNA libraries are not entirely independent, because more than one library may be obtained from a single subject or tissue. Nor are they entirely identically sampled, because different numbers of cDNAs may be sequenced from each library. The number of cDNAs sequenced typically ranges from 5,000 to 10,000 cDNAs per library. In addition, because a Fisher exact coexpression probability is calculated for each gene versus 41,419 other assembled genes, a Bonferroni correction for multiple statistical tests is necessary.

Using the method of the present invention, we have identified nine novel genes that exhibit strong association, or coexpression, with known genes that are specific to kidney disease. These known kidney disease-associated genes include uromodulin, NKCC2, NCCT, aldolase B, ROMK1, ATP1G1, PDZK1, NPT-1, calbindin, kininogen, and CIC-Kb. The results presented in Table 4 show that the expression of the nine novel genes have direct or indirect association with the expression of known kidney disease-associated genes. Therefore, the novel genes can potentially be used in diagnosis, treatment, prognosis, or prevention of diseases of the kidney or in the evaluation of therapies for diseases of the kidney. Further, the gene products of the nine novel genes are either potential therapeutic proteins or targets of therapeutics against diseases of the kidney.

Therefore, in one embodiment, the present invention encompasses a polynucleotide sequence comprising the sequence of SEQ ID NO:1–9. These nine polynucleotides are shown by the method of the present invention to have strong coexpression association with known kidney disease-associated genes and with each other. The invention also encompasses a variant of the polynucleotide sequence, its complement, or 18 consecutive nucleotides of a sequence provided in the above described sequences. Variant polynucleotide sequences typically have at least about 75%, more preferably at least about 85%, and most preferably at least about 95% polynucleotide sequence identity to NSEQ.

NSEQ or the encoded PSEQ may be used to search against the GenBank primate (pri), rodent (rod), mammalian (mam), vertebrate (vrtp), and eukaryote (eukp) databases, SwissProt, BLOCKS (Bairoch et al. (1997) Nucleic Acids Res. 25:217–221), PFAM, and other databases that contain previously identified and annotated motifs, sequences, and gene functions. Methods that search for primary sequence patterns with secondary structure gap penalties (Smith et al. (1992) Protein Engineering 5:35–51) as well as algorithms such as Basic Local Alignment Search Tool (BLAST; Altschul (1993) J. Mol. Evol. 36:290–300; Altschul et al. (1990) J. Mol. Biol. 215:403–410), BLOCKS (Henikoff and Henikoff(1991) Nucleic Acids Res. 19:6565–6572), Hidden Markov Models (HMM; Eddy (1996) Cur. Opin. Str. Biol. 6:361–365; Sonnhammer et al. (1997) Proteins 28:405–420), and the like, can be used to manipulate and analyze nucleotide and amino acid sequences. These databases, algorithms and other methods are well known in he art and are described in Ausubel et al. (1997; *Short Protocols in Molecular Biology*, John Wiley & Sons, New York N.Y., unit 7.7) and in Meyers (1995; *Molecular Biology and Biotechnology*, Wiley VCH, New York N.Y., p 856–853).

Also encompassed by the invention are polynucleotide sequences that are capable of hybridizing to SEQ ID NO:1–9, and fragments thereof under stringent conditions. Stringent conditions can be defined by salt concentration, temperature, and other chemicals and conditions well known in the art. Suitable conditions can be selected, for example, by varying the concentrations of salt in the prehybridization, hybridization, and wash solutions or by varying the hybridization and wash temperatures. With some substrates, the temperature can be decreased by adding formamide to the prehybridization and hybridization solutions.

Hybridization can be performed at low stringency, with buffers such as 5×SSC with 1% sodium dodecyl sulfate (SDS) at 60° C., which permits complex formation between two nucleic acid sequences that contain some mismatches. Subsequent washes are performed at higher stringency with buffers such as 0.2×SSC with 0.1% SDS at either 45° C. (medium stringency) or 68° C. (high stringency), to maintain hybridization of only those complexes that contain completely complementary sequences. Background signals can be reduced by the use of detergents such as SDS, Sarcosyl, or Triton X-100, and/or a blocking agent, such as salmon sperm DNA. Hybridization methods are described in detail in Ausubel (supra, units 2.8–2.11, 3.18–3.19 and 4–6–4.9) and Sambrook et al. (1989; *Molecular Cloning, A Laboratory Manual*, Cold Spring Harbor Press, Plainview N.Y.)

NSEQ can be extended utilizing a partial nucleotide sequence and employing various PCR-based methods known in the art to detect upstream sequences such as promoters and other regulatory elements. (See, e.g., Dieffenbach and Dveksler (1995) *PCR Primer, a Laboratory Manual*, Cold Spring Harbor Press, Plainview N.Y.) Additionally, one may use an XL-PCR kit (Perkin Elmer, Norwalk Conn.), nested primers, and commercially available cDNA libraries (Life Technologies, Rockville Md.) or genomic libraries (Clontech, Palo Alto Calif.) to extend the sequence. For all PCR-based methods, primers may be designed using commercially available software, such as OLIGO 4.06 Primer Analysis software (National Biosciences, Plymouth Minn.) or another appropriate program, to be about 18 to 30 nucleotides in length, to have a GC content of about 50%, and to form a hybridization complex at temperatures of about 68° C. to 72° C.

In another aspect of the invention, NSEQ can be cloned in recombinant DNA molecules that direct the expression of PSEQ, or structural or functional portions thereof, in appropriate host cells. Due to the inherent degeneracy of the genetic code, other DNA sequences which encode substantially the same or a functionally equivalent amino acid sequence may be produced and used to express the polypeptide encoded by NSEQ. The nucleotide sequences of the present invention can be engineered using methods generally known in the art in order to alter the nucleotide sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference., produce splice variants, and so forth.

In order to express a biologically active protein, NSEQ, or derivatives thereof, may be inserted into an appropriate expression vector, i.e., a vector which contains the necessary elements for transcriptional and translational control of the inserted coding sequence in a particular host. These elements include regulatory sequences, such as enhancers, constitutive and inducible promoters, and 5' and 3' untranslated regions. Methods which are well known to those skilled in the art may be used to construct such expression vectors. These methods include in vitro recombinant DNA techniques, synthetic techniques, and in vivo genetic recombination. (See, e.g., Sambrook, supra; and Ausubel, supra.)

A variety of expression vector/host cell systems may be utilized to express NSEQ. These include, but are not limited to, microorganisms such as bacteria transformed with recombinant bacteriophage, plasmid, or cosmid DNA expression vectors; yeast transformed with yeast expression vectors; insect cell systems infected with baculovirus vectors; plant cell systems transformed with viral or bacterial expression vectors; or animal cell systems. For long term production of recombinant proteins in mammalian systems, stable expression in cell lines is preferred. For example, NSEQ can be transformed into cell lines using expression vectors which may contain viral origins of replication and/or endogenous expression elements and a selectable or visible marker gene on the same or on a separate vector. The invention is not to be limited by the vector or host cell employed.

In general, host cells that contain NSEQ and that express PSE,Q may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences. Immunological niethods for detecting and measuring the expression of PSEQ using either specific polyclonal or monoclonal antibodies are known in the art. Examples of such techniques include enzyme-linked immunosorbent assays (ELISAs), radioimmunoassays (RIAs), and fluorescence activated cell sorting (FACS).

Host cells transformed with NSEQ may be cultured under conditions suitable for the expression and recovery of the protein from cell culture. The protein produced by a transgenic cell may be secreted or retained intracellularly depending on the sequence and/or the vector used. As will be understood by those of skill in the art, expression vectors containing NSEQ may be designed to contain signal sequences which direct secretion of the protein through a prokaryotic or eukaryotic cell membrane.

In addition, a host cell strain may be chosen for its ability to :modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and W138) are available from the American Type Culture Collection (ATCC, Bethesda Md.) and may be chosen to ensure the correct modification and processing of the expressed protein.

In another embodiment of the invention, natural, modified, or recombinant nucleic acid sequences are ligated to a heterologous sequence resulting in translation of a fusion protein containing heterologous protein moieties in any of the aforementioned host systems. Such heterologous protein moieties facilitate purification of fusion proteins using commercially available affinity matrices. Such moieties include, but are not limited to, glutathione S-transferase, maitose binding protein, thioredoxin, calmodulin binding peptide, 6-His, FLAG, c-myc, hemaglutinin, and monoclonal antibody epitopes.

In another embodiment, the nucleic acid sequences are synthesized, in whole or in part, using chemical or enzymatic methods well known in the art (Caruthers et al. (1980) Nucleic. Acids Symp. Ser.(7) 215–233; Ausubel, supra). For example, peptide synthesis can be performed using various solid-phase techniques (Roberge et al. (1995) Science 269:202–204), and machines such as the ABI 431A Peptide synthesizer (Perkin Elmer) can be used to automate synthesis. If desired, the amino acid sequence may be altered during synthesis and/or combined with sequences from other proteins to produce a variant protein.

In another embodiment, the invention entails a substantially purified polypeptide comprising the amino acid sequence selected from the group consisting of SEQ ID NO:10–12 and fragments thereof.

Diagnostics and Therapeutics

The polynucleotide sequences can be used in diagnosis, prognosis, treatment, prevention, and evaluation of therapies for diseases of the kidney including, but not limited, Bartter's syndrome, Gitelman syndrome, nephrolithiasis, renal amyloidosis, hypertension; primary aldosteronism; Addison's disease; renal failure; glomerulonephritis; chronic glomerulonephritis; tubulointerstitial nephritis; cystic disorders of the kidney and dysplastic malformations such as polycystic disease, renal dysplasias, and cortical or medullary cysts; inherited polycystic renal diseases (PRD), such as recessive and autosomal dominant PRD; medullary cystic disease; medullary sponge kidney and tubular dysplasia; Alport's syndrome; non-renal cancers which affect renal physiology, such as bronchogenic tumors of the lungs or tumors of the basal region of the brain; multiple myeloma; adenocarcinomas of the kidney; metastatic renal carcinoma; in addition, nephrotoxic disorders include any functional or morphologic change in the kidney produced by any pharmaceutical, chemical, or biological agent that is ingested, injected, inhaled, or absorbed.

In one preferred embodiment, the polynucleotide sequences are used for diagnostic purposes to determine the absence, presence, and excess expression of the protein. The polynucleotides may be at least 18 nucleotides long and consist of complementary RNA and DNA molecules, branched nucleic acids, and/or peptide nucleic acids (PNAs). In one alternative, the polynucleotides are used to detect and quantify gene expression in samples in which expression of NSEQ is correlated with disease. In another alternative, NSEQ can be used to detect genetic polymorphisms associated with a disease. These polymorphisms may be detected in the transcript cDNA.

The specificity of the probe is determined by whether it is made from a unique region, a regulatory region, or from a conserved motif. Both probe specificity and the stringency of diagnostic hybridization or amplification (maximal, high, intermediate, or low) will determine whether the probe identifies only naturally occurring, exactly complementary sequence;, allelic variants, or related sequences. Probes designed to detect related sequences should preferably have at least 75% sequence identity to any of the nucleic acid sequences encoding PSEQ.

Methods for producing hybridization probes include the cloning of nucleic acid sequences into vectors for the production of mRNA probes. Such vectors are known in the art, are commercially available, and may be used to synthesize RNA probes in vitro by adding appropriate RNA polymerases and labeled nucleotides. Hybridization probes may incorporate nucleotides labeled by a variety of reporter groups including, but not limited to, radionuclides such as $^{32}P$ or $^{35}S$, enzymatic labels such as alkaline phosphatase coupled to the probe via avidin/biotin coupling systems, fluorescent labels, and the like. The labeled polynucleotide sequences may be used in Southern or northern analysis, dot blot, or other membrane-based technologies; in PCR technologies; and in microarrays utilizing samples from subjects to detect altered PSEQ expression.

NSEQ can be labeled by standard methods and added to a sample from a subject under conditions suitable for the formation and detection of hybridization complexes. After incubation the sample is washed, and the signal associated with hybrid complex formation is quantitated and compared with a standard value. Standard values are derived from any control sample, typically one that is free of the suspect disease. If the amount of signal in the subject sample is altered in comparison to the standard value, then the presence of altered levels of expression in the sample indicates the presence of the disease. Qualitative and quantitative methods for comparing the hybridization complexes formed in subject samples with previously established standards are well known in the art.

Such assays may also be used to evaluate the efficacy of a particular therapeutic treatment regimen in animal studies, in clinical trials, or to monitor the treatment of an individual subject. Once the presence of disease is established and a treatment protocol is initiated, hybridization or amplification assays can be repeated on a regular basis to determine if the level of expression in the subject begins to approximate that which is observed in a healthy subject. The results obtained from successive assays may be used to show the efficacy of treatment over a period ranging from several days to many years.

The polynucleotides may be used for the diagnosis of a variety of diseases associated with the kidney. These include, but are not limited to, Bartter's syndrome, Gitelman syndrome, nephrolithiasis, renal amyloidosis, hypertension; primary aldosteronism; Addison's cLisease; renal failure; glomerulonephritis; chronic glomerulonephritis; tubulointerstitial nephritis; cystic disorders of the kidney and dysplastic malformations such as polycystic disease, renal dysplasias, and cortical or medullary cysts; inherited polycystic renal diseases (PRD), such as recessive and autosomal dominant PRD; medullary cystic disease; medullary sponge kidney and tubular dysplasia; Alport's syndrome; non-renal cancers which affect renal physiology, such as bronchogenic tumors of the lungs or tumors of the basal region of the brain; multiple myeloma; adenocarcinomas of the kidney; metastatic renal carcinoma; in addition, nephrotoxic disorders include any functional or morphologic change in the kidney produced by any pharmaceutical, chemical, or biological agent that is ingested, injected, inhaled, or absorbed.

The polynucleotides may also be used as targets in a microarray. The microarray can be used to monitor the expression patterns of large numbers of genes simultaneously and to identify splice variants, mutations, and polymorphisms. Information derived from analyses cf the expression patterns may be used to determine gene function, to understand the genetic basis of a disease, to diagnose a disease, and to develop and monitor the activities of therapeutic agents used to treat a disease. Microarrays may also be used to detect genetic diversity, single nucleotide polymorphisms which may characterize a particular population, at the genome level.

In yet another alternative, polynucleotides may be used to generate hybridization probes useful in mapping the naturally occurring genomic sequence. Fluorescent in situ hybridization (FISH) may be correlated with other physical chromosome mapping techniques and genetic map data as described in Heinz-Ulrich et al. (In: Meyers, supra, pp. 965–968).

In another embodiment, antibodies or antibody fragments comprising an antigen binding site that specifically binds PSEQ may be used for the diagnosis of diseases characterized by the over-or-under expression of PSEQ. A variety of protocols for measuring PSEQ, including ELISAs, RIAs, and FACS, are well known in the art and provide a basis for diagnosing altered or abnormal levels of expression. Standard values for PSEQ expression are established by combining samples taken from healthy subjects, preferably human, with antibody to PSEQ under conditions suitable for complex formation The amount of complex formation may be quantitated by various methods, preferably by photometric means. Quantities of PSEQ expressed in disease samples are compared with standard values. Deviation between standard and subject values establishes the parameters for diagnosing or monitoring disease. Alternatively, one may use competitive drug screening assays in which neutralizing antibodies capable of binding PSEQ specifically compete with a test compound for binding the protein. Antibodies can be used to detect the presence of any peptide which shares one or more antigenic determinants with PSEQ. In one aspect, the anti-PSEQ antibodies of the present invention can te used for treatment or monitoring therapeutic treatment for diseases of the kidney.

In another aspect, the NSEQ, or its complement, may be used therapeutically for the purpose of expressing mRNA and protein, or conversely to block transcription or translation of the mRNA. Expression vectors may be constructed using elements from retroviruses, adenoviruses, herpes or vaccinia viruses, or bacterial plasmids, and the like. These vectors may be used for delivery of nucleotide sequences to a particular target organ, tissue, or cell population. Methods well known to those skilled in the art can be used to construct vectors to express nucleic acid sequences or their complements. (See, e.g., Maulik et al. (1997) *Molecular Biotechnology, Therapeutic Applications and Strategies*, Wiley-Liss, New York N.Y.) Alternatively, NSEQ, or its complement, may be used for somatic cell or stem cell gene therapy. Vectors may be introduced in vivo, in vitro, and ex vivo. For ex vivo therapy, vectors are introduced into stem cells taken from the subject, and the resulting transgenic cells are clonally propagated for autologous transplant back into that same subject. Delivery of NSEQ by transfection, liposome injections, or polycationic amino polymers may be achieved using methods which are well known in the art. (See, e.g., Goldman et al. (1997) Nature Biotechnology 15:462–466.) Additionally, endogenous NSEQ expression may be inactivated using homologous recombination methods which insert an inactive gene sequence into the coding region or other appropriate targeted region of NSEQ. (See, e.g. Thomas et al. (1987) Cell 51: 503–512.)

Vectors containing NSEQ can be transformed into a cell or tissue to express a missing protein or to replace a nonfunctional protein. Similarly a vector constructed to express the complement of NSEQ can be transformed into a cell to downregulate the overexpression of PSEQ. Complementary or antisense sequences may consist of an oligonucleotide derived from the transcription initiation site; nucleotides between about positions −10 and +10 from the ATG are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee et al. In: Huber and Carr (1994) *Molecular and Immunologic Approaches*, Futura Publishing Co., Mt. Kisco N.Y., pp. 163–177.)

Ribozymes, enzymatic RNA molecules, may also be used to c atalyze the cleavage of mRNA and decrease the levels of particular mRNAs, such as those comprising the polynucleotide sequences of the invention. (See, e.g., Rossi (1994) Current Biology 4: 469–471.) Ribozymes may cleave mRNA at specific cleavage sites. Alternatively, ribozymes may cleave mRNAs at locations dictated by flanking regions that form complementary base pairs with the target mRNA. The construction and production of ribozymes is well known in the art and is described in Meyers (supra).

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiester linkages within the backbone of the molecule. Alternatively, nontraditional bases such as inosine, queosine, and wybutosine, as well as acetyl-, methyl-, thio-, and similarly modified forms of adenine, cytidine, guanine, thymine, and uridine which are not as easily recognized by endogerious endonucleases, may be included.

Further, an antagonist, or an antibody that binds specifically to PSEQ may be administered to a subject to treat or prevent a disease of the kidney. The antagonist, antibody, or fragment may be used directly to inhibit the activity of the protein or indirectly to deliver a therapeutic agent to cells or tissues which express the PSEQ. An immunoconjugate comprising a PSEQ binding site of the antibody or the antagonist and a therapeutic agent may be administered to a subject in need to treat or prevent disease. The therapeutic agent may be a cytotoxic agent selected from a group including, but not limited to, abrin, ricin, doxorubicin, daunorubicin, taxol, ethidium bromide, mitomy in, etoposide, tenoposide, vincristine, vinblastine, colchicine, dihydroxy anthracin dione, actinomycin D, diphteria toxin, Pseudomonas exotoxin A and 40, radioisotopes, and glucocorticoid.

Antibodies to PSEQ may be generated using methods that are well known in the art. Such antibodies may include, but are not limited to, polyclonal, monoclonal, chimeric, and single chain antibodies, Fab fragments, and fragments produced by a Fab expression library. Neutralizing antibodies, such as those which inhibit dimer formation, are especially preferred for therapeutic use. Monoclonal antibodies to PSEQ may be prepared using any technique which provides for the production of antibody molecules by continuous cell lines in culture. These include, but are not limited to, the hybridoma, the human B-cell hybridoma, and the EBV-hybridoma techniques. In addition, techniques developed for the production of chimeric antibodies can be used. (See, e.g., Pound (1998) *Immunochemical Protocols*, Methods Mol. Biol. Vol. 80.) Alternatively, techniques described for the production of single chain antibodies may be employed. Antibody fragments which contain specific binding sites for PSEQ may also be generated. Various immunoassays may be used to identify antibodies having the desired specificity. Numerous protocols for competitive binding or immunoradiometric assays using either polyclonal or monoclonal antibodies with established specificities are well known in the art.

Yet further, an agonist of PSEQ may be administered to a subject to treat or prevent a disease associated with decreased expression, longevity or activity of PSEQ.

An additional aspect of the invention relates to the administration of a pharmaceutical or sterile composition, in conjunction with a pharmaceutically acceptable carrier, for any of the therapeutic applications discussed above. Such pharmaceutical compositions may consist of PSEQ or antibodies, mimetics, agonists, antagonists, or inhibitors of the polypeptide. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a subject alone or in combination with other agents, drugs, or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton Pa.).

For any compound, the therapeutically effective dose can be estimated initially either in cell culture assays or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient which ameliorates the symptoms or condition. Therapeutic efficacy and toxicity may be determined by standard pharmaceutical procedures in cell cultures or with experimental animals, such as by calculating and contrasting the $ED_{50}$ (the dose therapeutically effective in 50% of the population) and $LD_{50}$ (the dose lethal to 50% of the population) statistics. Any of the therapeutic compositions described above may be applied to any subject in need of such therapy, including, but not limited to, mammals such as dogs, cats, cows, horses, rabbits, monkeys, and most preferably, humans.

EXAMPLES

It is to be understood that this invention is not limited to the particular devices, machines, materials and methods described. Although particular embodiments are described, equivalent embodiments may be used to practice the invention. The described embodiments are not intended to limit the scope of the invention which is limited only by the appended claims. The examples below are provided to illustrate the subject invention and are not included for the purpose of limiting the invention.

I cDNA Library Construction

The KIDNNOT19 library, in which Incyte clones 2673009 ard 2675922 were discovered, was constructed from RNA isolated from kidney tissue removed from a 65-year-old male during an exploratory laparotomy and nephroureterectomy. Pathology for the associated tumor tissue indicated a grade 1 renal cell carcinoma, clear cell type, forming a variegated mass situated within the upper pole of the left kidney. Patient presented with abdominal pain. Patient history included benign hypertension. Patient medications included verapamil, lisinopril, and aspirin. The frozen tissue was homogenized and lysed in TRIZOL reagent (1.0 gm tissue/10 ml TRIZOL; Life Technologies), a monophasic solution of phenol and guanidine isothiocyante, using a POLYTRON homogenizer (PT-3000; Brinkmann Instruments, Westbury N.Y.). Following homogenization, chloroform was added to the homogenate (at a ratio of 1:5 chlororform:homogenate, v/v) and the phases separated by centrifugation. The aqueous phase was removed to a fresh tube and mixed with isopropanol. Precipitated RNA was resuspended in DEPC-treated water and treated with DNAse for 25 minutes at 37° C. The RNA was re-extracted with acid phenol-chloroform pH 4.7 and precipitated with 0.3M sodium acetate and 2.5 volumes 100% ethanol. The mRNA was isolated using the OLIGOTEX kit (QIAGEN, Valencia Calif.) and used to construct the cDNA library.

The mRNA was handled according to the recommended protocols in the SUPERSCRIPT plasmid system (Life Technologies). The cDNAs were fractionated on a SEPHAROSE CL4B column (Amersham Pharmacia Biotech, Piscataway N.J.), and those cDNAs exceeding 400 bp were ligated into pINCY 1 plasmid (Incyte Pharmaceuticals, Palo Alto Calif.). The plasmid was subsequently transformed into DH5 α competent cells (Life Technologies).

II Isolation and Sequencing of cDNA Clones

Plasmid DNA was released from the cells and purified using the REAL Prep 96 plasmid kit (QIAGEN). This kit enabled the simultaneous purification of 96 samples in a 96-well block using multi-channel reagent dispensers. The recommended protocol was employed except for the following changes: 1) the bacteria were cultured in 1 ml of sterile Terrific Brolh (Life Technologies) with carbenicillin at 25 mg/L and glycerol at 0.4%; 2) after inoculation, the cultures were incubated for 19 hours; at the end of incubation, the cells were lysed with 0.3 ml of lysis buffer; and 3) following isopropanol precipitation, the plasmid DNA pellet was resuspended in 0.1 ml of distilled water, and samples were transferred to a 96-well block for storage at 4° C.

The cDNAs were prepared using a Hamilton Micro Lab 2200 (Hamilton, Reno Nev.) in combination with DNA ENGINE thermal cycler (PTC200; MJ Research, Watertown Mass.). cDNAs were sequenced by the method of Sanger et al. (1975, J. Mol. Biol. 94:441f) using ABI PRISM 377 DNA sequencers (Perkin Elmer) or MEGABASE 1000 sequencing systems (Amersham Pharmacia Biotech).

Most of the sequences disclosed herein were sequenced using standard ABI protocols and kits (Perkin Elmer). The solution volumes were used at 0.25×1.0×concentrations. Some of the sequences disclosed herein were sequenced using solutions and dyes from Amersham Pharmacia Biotech.

III Selection, Assembly, and Characterization of Sequences

The sequences used for coexpression analysis were assembled from EST sequences, 5' and 3' longread sequences, and full length coding sequences. Selected assembled sequences were expressed in at least three cDNA libraries.

The assembly process is described as follows. EST sequence chromatograms were processed and verified. Quality scores were obtained using PHRED (Ewing et al. (1998) Genome Res. 8:175–185; Ewing and Green (1998) Genome Res. 8:186–194), and edited sequences were loaded into a relational database management system (RDBMS). The sequences were clustered using BLAST with a product score of 50. All clusters of two or more sequences created a bin, and each bin with its resident sequences represents one transcribed gene.

Assembly of the component sequences within each bin was performed using a modification of Phrap, a publicly available program for assembling DNA fragments (Green, P. University of Washington, Seattle Wash.). Bins that showed 82% identity from a local pair-wise alignment between any of the consensus sequences were merged.

Bins were annotated by screening the consensus sequence in each bin against public databases, such as GBpri and GenPept from NCBI. The annotation process involved a FASTn screen against the GBpri database in GenBank. Those hits with a percent identity of greater than or equal to 75% and an alignment length of greater than or equal to 100 base pairs were recorded as homolog hits. The residual unannotated sequences were screened by FASTx against GenPept. Those hits with an E value of less than or equal to $10^{-8}$ were recorded as homolog hits.

Sequences were then reclustered using BLASTn and Cross-Match, a program for rapid protein and nucleic acid sequence comparison and database search (Green, supra), sequentially. Any BLAST alignment between a sequence and a consensus sequence with a score greater than 150 was realigned using cross-match. The sequence was added to the bin whose consensus sequence gave the highest Smith-Waterman score (Smith et al. (1992) Protein Engineering 5:35–51) amongst local alignments with at least 82% identity. Non-matching sequences were moved into new bins, and assembly processes were performed for the new bins.

IV Coexpression Analyses of Known Kidney Disease-Associated Genes

Fourteen known kidney disease-associated genes were selected to identify novel genes that are closely associated with diseases of the kidney. These known genes were uromodulin, NKCC2, NCCT, aldolase B, ROMK1, ATP1G1, PDZK1, NPT-1, calbindin, kininogen, and ClC-Kb. The kidney disease-associated genes which were examined in this analysis and brief descriptions of their functions are listed in Table 3.

TABLE 3

Descriptions of Known Kidney Disease-Associated Genes

| GENE | DESCRIPTION AND REFERENCES |
|---|---|
| Uromodulin | Tamm-Horsfall glycoprotein; immuno-suppressive; binds IL-1α, β, TNF marker for distal tubular function; marker for chronic ifosfamide (antineoplastic) nephrotoxicity, implicated in kidney stone formation (Hallson et al. (1997) Br. J. Urol. 80: 533–538; MacLean et al. (1998) Cancer Chemother. Pharmacol. 41: 413–416; Torffvit et al. (1998) Nephron 79: 167–172) |

TABLE 3-continued

Descriptions of Known Kidney Disease-Associated Genes

| GENE | DESCRIPTION AND REFERENCES |
|---|---|
| NKCC2 | Bumetanide-sensitive Na (K$^+$)-Cl$_2$ co-transporter; mutant NKCC2 leads to neonatal Bartter's syndrome (hypokalaemic alkalosis, low blood pressure, hypercalciuria); implicated in autosomal dominant polycystic kidney disease (Simon et al. (1996) Nat. Genet. 13: 183–188; Sullivan et al. (1998) Physiol. Rev. 78: 1165–1191) |
| NCCT | Thiazide-sensitive Na (K$^+$)-Cl$_2$ co-transporter; mutant NCCT leads to Gitelman syndrome (hypoalaemic alkalosis, hypotension, hypocalciuria) (Mastroianni et al. (1996) Am. J. Hum. Genet. 59: 1019–1026) |
| Aldolase B | Fructose-bisphosphate aldolase, mutation in aldolase B leads to fructose intolerance and hepatorenal toxicity (Ali et al. (1993) Q. J. Med. 86: 25–30; Ali et al. (1998) J. Med. Genet. 35: 353–365) |
| ROMK1 | Inwardly rectifying voltage-gated K$^+$ channel; mutation in ROMK1 leads to form of Bartter's syndrome (Yano et al. (1994) Mol. Pharmacol. 45: 854–860; Derst et al. (1997) Biochem. Biophys. Res. Commun. 230: 641–645) |
| ATP1G1 | Na$^+$/K$^+$-ATPase gamma subunit; required for acquisition of fluid transport capacity (Jones et al. (1997) J. Cell Biol. 139: 1545–1552; Kim et al. (1997) Biochim. Biophys. Acta 1350: 133–135) |
| PDZK1 | PDZ domain containing protein; co-localizes with ion channels (Kocher et al. (1998) Lab. Invest. 78: 117–125) |
| NPT-1 | Na$^+$-dependent phosphate co-transporter; candidate for hereditary hypophosphatemia with hypercalciuria (Miyamoto et al. (1995) Biochem. J. 305: 81–85; Miyamoto et al. (1995) Tokushima J. Exp. Med. 42: 5–9) |
| Calbindin | Calcium-binding protein, vitamin D-dependent; excess protein levels in spontaneously hypertensive rats; decreased protein level associated with cyclosporin A nephrotoxicity in kidney transplant patients (Kamijo et al. (1996) Kidney Int. Suppl. 55: S166–168; Aicher et al. (1998) Electrophoresis 19: 1988–2003) |
| Kininogen | Cysteine protease inhibitor; regulates blood pressure in conjunction with renal kallikrein (Sharma et al. (1996) Gen. Pharmacol. 27: 55–63) |
| ClC-Kb | Chloride channel; mutations lead to classic Bartter's syndrome (Rodriguez-Soriano (1998) Pediatr. Nephrol. 12: 315–327) |

From a total of 41,419 assembled gene sequences, we have identified nine novel genes that show strong association with 11 known kidney disease-associated genes. final nine kidney disease genes. Details of the expression patterns for the 11 known and nine novel kidney disease genes are presented in Table 4.

TABLE 4

Co-Expression of Nine Novel Genes and 11 Known Kidney Cancer Genes (–log p)

| # | Name | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|---|
| 1 | Aldolase B | | | | | | | | | | | | | | | | | | | |
| 2 | PDZK1 | 9 | | | | | | | | | | | | | | | | | | |
| 3 | ATP1G1 | 10 | 13 | | | | | | | | | | | | | | | | | |
| 4 | Kininogen | 21 | 9 | 6 | | | | | | | | | | | | | | | | |
| 5 | NKCC2 | 7 | 10 | 7 | 6 | | | | | | | | | | | | | | | |
| 6 | NCCT | 5 | 9 | 10 | 6 | 10 | | | | | | | | | | | | | | |
| 7 | NPT-1 | 1 | 7 | 6 | 4 | 0 | 1 | | | | | | | | | | | | | |
| 8 | Uromodulin | 9 | 13 | 12 | 7 | 12 | 13 | 2 | | | | | | | | | | | | |
| 9 | ROMK1 | 6 | 8 | 7 | 9 | 6 | 7 | 1 | 9 | | | | | | | | | | | |
| 10 | ClC-Kb | 5 | 6 | 6 | 5 | 6 | 9 | 0 | 8 | 8 | | | | | | | | | | |
| 11 | Calbindin | 3 | 7 | 4 | 5 | 8 | 7 | 1 | 8 | 5 | 4 | | | | | | | | | |
| 12 | 2675922 | 4 | 5 | 5 | 4 | 7 | 7 | 0 | 6 | 3 | 4 | 4 | | | | | | | | |
| 13 | 3534377 | 4 | 6 | 5 | 7 | 8 | 8 | 0 | 7 | 6 | 5 | 5 | 6 | | | | | | | |
| 14 | 3481942 | 3 | 7 | 6 | 5 | 4 | 5 | 3 | 5 | 8 | 4 | 6 | 3 | 6 | | | | | | |
| 15 | 2911650 | 1 | 9 | 4 | 2 | 7 | 6 | 3 | 8 | 3 | 3 | 5 | 1 | 1 | 3 | | | | | |
| 16 | 1900433 | 4 | 6 | 5 | 5 | 8 | 9 | 0 | 7 | 7 | 10 | 5 | 5 | 6 | 5 | 4 | | | | |
| 17 | 2580580 | 3 | 9 | 7 | 3 | 3 | 5 | 6 | 5 | 5 | 3 | 3 | 2 | 3 | 6 | 3 | 3 | | | |
| 18 | 2673009 | 5 | 12 | 10 | 5 | 7 | 7 | 4 | 7 | 6 | 5 | 6 | 7 | 8 | 9 | 4 | 6 | 6 | | |
| 19 | 1399234 | 6 | 8 | 5 | 7 | 7 | 6 | 1 | 8 | 8 | 4 | 5 | 4 | 6 | 5 | 2 | 4 | 3 | 5 | |
| 20 | 1867351 | 1 | 7 | 3 | 2 | 1 | 1 | 6 | 3 | 3 | 1 | 1 | 1 | 1 | 3 | 2 | 1 | 4 | 3 | 2 |

Initially, the degree of association was measured by probability values using a cutoff p value less than 0.00001. The sequences were further examined to ensure that the genes that passed the probability test had strong association with known kidney disease-associated genes. The process was reiterated so that the initial 41,419 genes were reduced to the We examined genes that are coexpressed with the 11 known kidney disease-associated genes, and identified nine novel genes that are strongly coexpressed. Each of the nine novel genes is coexpressed with at least one of the 11 known genes with a p-value of less than 10e-05. The coexpression of the nine novel genes with the 11 known genes are shown in Table 4. The entries in Table 4 are the negative log of the p-value (−log p) for the coexpression of the two genes. The novel genes identified are listed in the table by their Incyte clone numbers, and the known genes, by their names or abbreviations shown in Table 3. For convenience, all the genes in table 4 are assigned an identifying number, 1 to 20.

V Novel Genes Associated with Kidney Diseases

Using the co-expression analysis method, we have identified nine novel genes that exhibit strong association, or co-expression, with 11 known kidney disease-associated genes.

Nucleic acids comprising the consensus sequences of SEQ ID NO:1–9 of the present invention were first identified from Incyte Clones 2675922, 3534377, 3481942, 2911650, 1900433, 2580580, 2673009, 1399234, and 1867351, respectively, and assembled as described in Example III. BLAST was performed for SEQ ID NO:1–9 as described in Example VI. SEQ ID NO:1–9 were translated and sequence identity was sought via motif searches and BLAST comparison to known sequences. SEQ ID NO:10–12 of the present invention were encoded by the nucleic acids of SEQ ID NO:3, SEQ ID NO:5, and SEQ ID NO:7, respectively. SEQ ID NO:10–12 were also analyzed using BLAST and other motif search tools as disclosed in Example VI. Analyses of the novel genes is as follows.

SEQ ID NO:1 (Incyte clone 2675922) is 613 nucleotides in length and has no significant known homologs in any of the public databases described in this application. SEQ ID NO:2 (Incyte clone 3534377) is 618 nucleotides in length and has no significant known homologs in any of the public databases described in this application. SEQ ID NO:3 (Incyte clone 3481942) is 512 nucleotides in length and has about 71% identity to the nucleic acid sequence of a rat kidney-specific protein (g3127192). SEQ ID NO:4 (Incyte clone 2911650) is 999 nucleotides in length and has no significant known homologs in any of the public databases described in this application. SEQ ID NO:5 (Incyte clone 1900433) is 616 nucleotides in length and has about 41% identity to the nucleic acid sequence of a human MAT8 protein (g1085025). SEQ ID NO:6 (Incyte clone 2580580) is 862 nucleotides in length and has no significant known homologs in any of the public databases described in this application. SEQ ID NO:7 (Incyte clone 2673009) is 1090 nucleotides in length and has no significant known homologs in any of the public databases described in this application. SEQ ID NO:8 (Incyte clone 1399234) is 1108 nucleotides in length and has no significant known homologs in any of the public databases described in this application. SEQ ID NO:9 (Incyte clone 1867351) is 1290 nucleotides in length and has no significant known homologs in any of the public databases described in this application. SEQ ID NO:10 has 139 amino acids which are encoded by SEQ ID NO:3 and has about 86% identity to the amino acid sequence of a rat kidney-specific protein (g3127193). Motif analyses of SEQ ID NO:10 show two potential phosphorylation sites at residues S19 and T137. SEQ ID NO:11 has 89 amino acids which are encoded by SEQ ID NO:5 and has about 71% identity to the amino acid sequence of a mouse MAT8 protein (g 1085068). Motif analyses of SEQ ID NO:11 show three potential phosphorylation sites at residues T15, S58, and S66, as well as a signal peptide sequence from residues M1 through A19, and a MAT8 family signature sequence from residue D28 through Y63. SEQ ID NO:12 has 285 amino acids which are encoded by SEQ ID NO:7. Motif analyses of SEQ ID NO:12 show nine potential phosphorylation sites at residues S27, T43, S67, T72, S87, T160, Y179, T227, and S236.

VI Homology Searching for Kidney Disease Genes and Their Encoded Proteins

The polynucleotide sequences, SEQ ID NO:1–9, and polypeptide sequences, SEQ ID NO:10–12, were queried against databases derived from sources such as GenBank and SwissProt. These databases, which contain previously identified and annotated sequences, were searched for regions of similarity using BLAST (Altschul, supra). BLAST searched for matches and reported only those that satisfied the probability thresholds of $10^{-25}$ or less for nucleotide sequences and $10^{-8}$ or less for polypeptide sequences.

The polypeptide sequences were also analyzed for known rriotif patterns using MOTIFS, SPSCAN, BLIMPS, and HMM-based protocols. MOTIFS (Genetics Computer Group, Madison Wis.) searches polypeptide sequences for patterns that match those defined in the Prosite Dictionary of Protein Sites and Patterns (Bairoch, supra) and displays the patterns found and their corresponding literature abstracts. SPSCAN (Genetics Computer Group) searches for potential signal peptide sequences using a weighted matrix method (Nielsen et al. (1997) Prot. Eng. 10:1–6). flits with a score of 5 or greater were considered. BLIMPS uses a weighted matrix analysis algorithm to search for sequence similarity between the polypeptide sequences and those contained in BLOCKS, a database consisting of short amino acid segments, or blocks of 3–60 amino acids in length, compiled from the PROSITE database (Henikoff; supra; Bairoch, supra), and those in PRINTS, a protein fingerprint database based on non-redundant sequences obtained from sources such as SwissProt, GenBank, PIR, and NRL-3D (Attwood et al. (1997) J. Chem. Inf. Comput. Sci. 37:417–424). For the purposes of the present invention, the BLIMPS searches reported matches with a cutoff score of 1000 or greater and a cutoff probability value of $1.0 \times 10^{-3}$. HMM-based protocols were based on a probabilistic approach and searched for consensus primary structures of gene families in the protein sequences (Eddy, supra; Sonnhammer, supra). More than 500 known protein families with cutoff scores ranging from 10 to 50 bits were selected for use in this invention.

VII Labeling of Probes and Hybridization Analyses Blotting

Polynucleotide sequences are isolated from a biological source and applied to a solid matrix (a blot) suitable for standard nucleic acid hybridization protocols by one of the following methods. A mixture of target nucleic acids is fractionated by electrophoresis through an 0.7% agarose gel in 1×TAE [40 mM Tris acetate, 2 mM ethylenediamine tetraacetic acid (EDTA)] running buffer and transferred to a nylon membrane by capillary transfer using 20×saline sodium citrate (SSC). Alternatively, the target nucleic acids are individually ligated to a vector and inserted into bacterial host cells to form a library. Target nucleic acids are arranged on a blot by one of the following methods. In the first method, bacterial cells containing individual clones are robotically picked and arranged on a nylon membrane. The membrane is placed on bacterial growth medium, LB agar containing carbenicillin, and incubated at 37° C. for 16 hours. Bacterial colonies are denatured, neutralized, and digested with proteinase K. Nylon membranes are exposed to UV irradiation in a STRATALINKER UV-crosslinker (Stratagene, La Jolla Calif.) to cross-link DNA to the membrane.

In the second method, target nucleic acids are amplified from bacterial vectors by thirty cycles of PCR using primers complementary to vector sequences flanking the insert. Amplified target nucleic acids are purified using SEPHACRYL-400 (Amersham Pharmacia Biotech). Purified target nucleic acids are robotically arrayed onto a glass microscope slide. The slide was previously coated with 0.05% aminopropyl silane (Sigma-Aldrich, St. Louis Mo.) and cured at 110° C. The arrayed glass slide (microarray) is exposed to UV irradiation in a STRATALINKER UV-crosslinker (Stratagene).

Probe Preparation cDNA probe sequences are made from mRNA templates. Five micrograms of mRNA is mixed with 1 g random primer (Life Technologies), incubated at 70° C. for 10 minutes, and lyophilized. The lyophilized sample is resuspended in 50 μl of 1×first strand buffer (cDNA Synthesis system; Life Technologies) containing a dNTP mix, [α-$^{32}$P]dCTP, dithiothreitol. and MMLV reverse transcriptase (Stratagene), and incubated at 42° C. for 1–2 hours. After incubation, the probe is diluted with 42 μl dH$_2$O, heated to 95° C. for 3 minutes, and cooled on ice. mRNA in the probe is removed by alkaline degradation. The probe is neutralized, and degraded mRNA and unincorporated nucleotides are removed using a PROBEQUANT G-50 MicroColumn (Amersham Pharmacia Biotech). Probes can be labeled with fluorescent markers, Cy3-dCTP or Cy5-dCTP (Amersham Pharmacia Biotech), in place of the radionuclide, [$^{32}$P]dCTP.

Hybridization

Hybridization is carried out at 65° C. in a hybridization buffer containing 0.5 M sodium phosphate (pH 7.2), 7% SDS, and 1 mM EDTA. After the blot is incubated in hybridization buffer at 65° C. for at least 2 hours, the buffer is replaced with 10 ml of fresh buffer containing the probe sequences. After incubation at 65° C. for 18 hours, the hybridization buffer is removed, and the blot is washed sequentially under increasingly stringent conditions, up to 40 mM sodium phosphate, 1% SDS, 1 mM EDTA at 65° C. To detect signal produced by a radiolabeled probe hybridized on a membrane, the blot is exposed to a PHOSPHO-RIMAGER cassette (Amersham Pharmacia Biotech), and the image is analyzed using IMAGEQUANT data analysis software (Amersham Pharmacia Biotech). To detect signals produced by a fluorescent probe hybridized on a microarray, the blot is examined by confocal laser microscopy, and images are collected and analyzed using GEMTOOLS gene expression analysis software (Incyte Pharmaceuticals).

VIII Production of Specific Antibodies

SEQ ID NO:10–12, or portions thereof, substantially purified using polyacrylamide gel electrophoresis or other purification techniques, is used to immunize rabbits and to produce antibodies using standard protocols as described in Pound (supra).

Alternatively, the amino acid sequence is analyzed using LASERGENE software (DNASTAR, Madison Wis.) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. Typically, oligopeptides 15 residues in length are synthesized using an ABI 431 A Peptide synthesizer (Perkin Elmer) using Fmoc-chemistry and coupled to keyhole limpet hemocyanin (KLH, Sigma-Aldrich) by reaction with N-maleimidobenzoyl-N-hydroxysuccinimide ester (Ausubel, supra) to increase immunogenicity. Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

What is claimed is:

1. A purified polynucleotide that is coexpressed with one or more known kidney disease-associated genes consisting of a nucleic acid sequence selected from the group consisting of SEQ ID NOs: 1, 2, 3 4, 5, 7, 8 and 9 and the complements thereof.

2. A expression vector containing a polynucleotide consisting of a nucleic acid sequence selected from the group consisting of SEQ ID NOs: 1–5 and 7–9.

3. A host cell culture, comprising the expression vector of claim 2.

4. A method for detecting expression of a polynucleotide that is coexpressed with one or more known kidney disease-associated genes, the method comprising the steps of:
 a) providing a sample;
 b) hybridizing the polynucleotide of claim 1 to nucleic acids of the sample under high stringency conditions to form one or more hybridization complexes;
 c) detecting hybridization complex formation, wherein complex formation indicates expression of the polynucleotide in the sample.

* * * * *

SEQUENCE LISTING

```
<160> NUMBER OF SEQ ID NOS: 12

<210> SEQ ID NO 1
<211> LENGTH: 613
<212> TYPE: DNA
<213> ORGANISM: Homo sapiens
<220> FEATURE: -
<223> OTHER INFORMATION: 2675922CT1

<400> SEQUENCE: 1
gggcaagggg cagttggtga acttgctgcc tccagagaac cttccctggt gtggaggcag     60
ccagggaccc aggatgctcc ggacctgtta cgtgctctgt tcccaagctg gtcccccctc    120 cagggctgg  cagtccctga gctttgatgg cggggccttc caccttaagg gcacaggaga    180
gctgacacgg gccttgctgg ttctccggct gtgtgcctgg cccccactcg tcactcacgg    240
gctgttgctc caggcctggt ctcggcgact cctgggctcc cggctctcag gcgcatttct    300
ccgagcatcc gtctatgggc agtttgtggc tggtgagaca gcagaggagg tgaagggctg    360
cgtgcagcac tgcggaccct cagcctccga ccactgctgg cagtgcccac tgaggaggag    420
ccggactctg ctgccaagag tgggtgagta gggagccagg gcccagggag gctgggagga    480
cgcaggaagg ggctttgctg ttcgggccct gacacctgct ggctgggcag tcacgcgtgg    540
tattacggga cctcggtgct atgctgcggt gtgtggacct gtcaagggggc ttctggagcc    600 cccagcctgg tga                                                       613
```

```
<210> SEQ ID NO 2
<211> LENGTH: 618
<212> TYPE: DNA
<213> ORGANISM: Homo sapiens
<220> FEATURE: -
<223> OTHER INFORMATION: 3534377CT1

<400> SEQUENCE: 2
gtagatgctt agactacttt gaactgaagt atgtgcagtc tgccatctca cattaaaatg      60
taggcatttt gtcaattgct tttctttcat ctgcacaaga ggaaggagag aacgaatcaa     120
tacaaccact cttttccttg agactgcaaa gaaaatggtt ctatagtttg atggttctac     180
ttcccagatg ctacctctca gatttattct caacagaaaa ttttttgatt acagcagacc     240
agatctttat ctgtcaataa gttaaaaaag ataatctggg ctggatgtgg tggctcactc     300
ctgtaattcc agcacttcgg gaggccaaga caggaggatt gcttgagccc aggaatttga     360
gaccagcctg gcaacatgg cgaaacccca atctctttat tttttgtttt tcgacataga      420
gtctcactct tgtcatccag ctggagtgc agtgccgtga tctcagctca ttgcactccg      480
cctcccgggt tcaagcaatt ctgcttcagc ctcccaagta gctgggatga caggcatgtg     540
tcaccatgcc cggccaattt tttttttttt ttcttgtatt tttagtagag acaggtttca     600
ccatgttggc caggctgg                                                    618

<210> SEQ ID NO 3
<211> LENGTH: 521
<212> TYPE: DNA
<213> ORGANISM: Homo sapiens
<220> FEATURE: -
<223> OTHER INFORMATION: 3481942CB1

<400> SEQUENCE: 3
tctggagctg ctggctggag aggagggtgg acgaagctct ctctagaaag acatcctgag      60
aggacttggc aggcctgaac atgcattggc tgcgaaaagt tcagggactt tgcaccctgt     120
ggggtactca gatgtccagc cgcactctct acattaatag taggcaactg gtgtccctgc     180
agtggggcca ccaggaagtg ccggccaagt ttaactttgc tagtgatgtg ttggatcact     240
gggctgacat ggagaaggct ggcaagcgac tcccaagccc agccctgtgg tgggtgaatg     300
ggaaggggaa ggaattaatg tggaatttca gagaactgag tgaaaacagc cagcaggcag     360
ccaacgtcct ctcgggagcc tgtggcctgc agcgtgggga tcgtgtggca gtggtgctgc     420
cccgagtgcc tgagtggtgg ctggtgatcc tgggctgcat tcgagcaggg ctcatccttta     480 tgcctggaac catcagatga gatccactga catactgtat a                         521

<210> SEQ ID NO 4
<211> LENGTH: 999
<212> TYPE: DNA
<213> ORGANISM: Homo sapiens
<220> FEATURE: -
<223> OTHER INFORMATION: 2911650CT1

<400> SEQUENCE: 4
tggtagtcat cagtgaaaga catttgaggt taagacagca agtccttgac aaatatgttc      60 atgtctatt ggttctagtt ctataaaaat atgaacattg ggactcagag aaaatgggga     120
aaataaagtg gattcaggtt atcagtgaaa tgatggtata gattacagca atctggata      180 tatattgatg ttactgcatt tgtaaatgtc ctcccattaa acagaaaatg tggctaaaat     240
ccctggcctg gaactgaact agtttaaggc aggtgtaaga atagtgggag gaaagtttgt     300
```

-continued

```
gaaagtttaa agaatgccct caatccatga acgagaggga ggatgttgtc tttaattatt      360
tagaaggttt ttttttcctt gtctgttgat aattttatgg aaggttgctt tagatctcca      420
ttccttaaaa aatattacat gtcagtgtag ttagatatta tctcttttag ttattatact      480
tgctattttt actgtatagt gtggtataat caacaaaaaa taatgccacg ggcatgttta      540 cacctttttct gttgcactat taaattcttt tcacagtatt catatcaatg ctaatttgaa     600
tgtgatgcca attaaaaatc ttgttcattt atattgtata tggtacaagg acgtagcata      660
agatccaaaa aaaattttgt attgtcattt agcatatcaa tttcagccaa atttggaaga      720
cttgatcatc ttatcttttg ctctacacac tcaaaacaaa tattgcagca gaaatatcac      780
cttaaaaata tcttatttta tatttagata atattgaaat cacagtctat taaaattgga      840
aatttaattc aaataaaaat caaacaaaat agttgtttca atttatctaa atatctggtc      900
ttaagagtgc cttaagagtg tctcgttttt aagagtgtct taaaaacgaa tatatgtata      960
agtcaacaaa tcatataata tgaaataaat agctctggg                              999
```

<210> SEQ ID NO 5
<211> LENGTH: 616
<212> TYPE: DNA
<213> ORGANISM: Homo sapiens
<220> FEATURE: -
<223> OTHER INFORMATION: 1900433CB1

<400> SEQUENCE: 5

```
gccagctcag gtgagccctc gccaaggtga cctcgcagga cactggtgaa ggagcagtga       60
ggaacctgca gagtcacaca gttgctgacc aattgagctg tgagcctgga gcagatccgt      120
gggctgcaga ccccgcccc agtgcctctc cccctgcagc cctgccctc gaactgtgac       180 atggagagag tgaccctggc ccttctccta ctggcaggcc tgactgcctt ggaagccaat      240
gacccatttg ccaataaaga cgatcccttc tactatgact ggaaaaacct gcagctgagc      300
ggactgatct gcggagggct cctggccatt gctgggatcg cggcagttct gagtggcaaa      360
tgcaaataca agagcagcca gaagcagcac agtcctgtac ctgagaaggc catcccactc      420
atcactccag gctctgccac tacttgctga gcacaggact ggcctccagg gatggcctga      480
agcctaacac tggcccccag cacctcctcc cctgggagcc cttatcctca aggaaggact      540
tctctccaag ggcaggctgt taggcccctt tctgatcagg aggcttcttt atgaattaaa      600
ctcgccccac cacccc                                                      616
```

<210> SEQ ID NO 6
<211> LENGTH: 862
<212> TYPE: DNA
<213> ORGANISM: Homo sapiens
<220> FEATURE: -
<223> OTHER INFORMATION: 2580580CT1

<400> SEQUENCE: 6

```
gttgcaattg cactactgat tttatcaggg atctggcaac gtagaagaaa gaacaaagaa       60
ccatctgaag tggatgacgc tgaagataag tgtgaaaaca tgatcacaat tgaaaatggc      120
atcccctctg atcccctgga catgaaggga gggcatatta atgatgcctt catgacagag      180
gatgagaggc tcacccctct ctgaagggct gttgttctgc ttcctcaaga aattaaacat      240
ttgtttctgt gtgactgctg agcatcctga ataccaaga gcagatcata tattttgttt       300
caccattctt cttttgtaat aaattttgaa tgtgcttgaa agtgaaaagc aatcaattat      360
acccaccaac accactgaaa tcataagcta ttcacgactc aaaatattct aaaatatttt      420
```

```
tctgacagta tagtgtataa atgtggtcat gtggtatttg tagttattga tttaagcatt    480
tttagaaata agatcaggca tatgtatata ttttcacact tcaaagacct aaggaaaaat    540
aaattttcca gtggagaata catataatat ggtgtagaaa tcattgaaaa tggatccttt    600
ttgacgatca cttatatcac tctgtatatg actaagtaaa caaaagtgag aagtaattat    660
tgtaaatgga tggataaaaa tggaattact catatacagg gtggaatttt atcctgttat    720
cacaccaaca gttgattata tattttctga atatcagccc ctaataggac aattctattt    780
gttgaccatt tctacaattt gtaaaagtcc aatctgtgct aacttaataa agtaataatc    840
atctcttaaa aaaaaaaaaa aa                                             862
```

<210> SEQ ID NO 7
<211> LENGTH: 1090
<212> TYPE: DNA
<213> ORGANISM: Homo sapiens
<220> FEATURE: -
<223> OTHER INFORMATION: 2673009CB1

<400> SEQUENCE: 7

```
tgccacctga gcgccgctcc ctctcaggat gaaggtgacg gtgggcccag acccttccct     60
ggtctaccga cctgatgtgg acccagaggt ggccaaagac aaggccagct tccgaaacta    120
cacgtcaggt cccctcctgg accgtgtctt caccacctac aagctcatgc acacgcacca    180
gacagtggac ttcgtcagga gcaagcatgc ccagtttggg ggcttctcct acaagaaaat    240
gacagtcatg gaggccgtgg acctgctgga tgggctggtg gatgagtcgg acccggacgt    300
agatttcccc aactccttcc atgccttcca gacagcggag ggcatccgga aggcccaccc    360
agacaaggac tggttccacc tcgtcgggct cctgcacgac ctggggaagg tcctggccct    420
gttcggggag ccccagtggg ctgtcgtcgg cgacaccttc cccgtcggat gccgtccgca    480
ggcctccgtg gttttctgcg actccacctt ccaggacaac cctgacctcc aggatcctcg    540
atacagcaca gagctcggga tgtatcagcc ccactgtggg ctcgacaggg tcctcatgtc    600
ctggggccat gatgagtaca tgtaccaggt gatgaagttt aacaagttct cactgccccc    660
tgaggctttc tacatgatcc ggttccactc cttctacccc tggcacacgg gccgcgacta    720
ccagcagctg tgcagccagc aggacctggc catgctgccc tgggtgcggg agttcaacaa    780
gttcgacctc tacaccaagt gcccggacct gccggacgtg acaagctgc ggccctacta    840 ccagggctc attgacaagt actgcctgg catcctgagc tggtgaccct cctgccaccc    900
aagctgctgc tggacctagg cctggccctc cgcctgcctg gagaggcctg gcctgggca    960 aacagccgcc atcagggttc acctcggtgg gggaccccac tcacccctt agggtcgcca   1020 ccctcacgg caacttgtgc ctggcgtcaa taaagacctg gaaggatgtt gtgcttctga   1080
aaaaaaaaaa                                                         1090
```

<210> SEQ ID NO 8
<211> LENGTH: 1108
<212> TYPE: DNA
<213> ORGANISM: Homo sapiens
<220> FEATURE: -
<223> OTHER INFORMATION: 1399234CT1

<400> SEQUENCE: 8

```
aaactgacct gccaggacg ccctgggaac aggggcgga gctccggcta gagggactc      60 ctgtgtgggc gggcaggtct ggagcctggg cccaggtgtg gcctgctggg ggacagctcc   120
```

-continued

```
gggggagagc tgtggggaga acagcggtct agggaggcag gaggcaggcg gcaggctcct    180
ccccagcagc ctgcagggca tcaggacaga gggggaagga ggagacagaa gggaaagaag    240
gagatagagg gggaaggagg aaacagcgcg gcttctgctg aagccagtac aagcctggtt    300
atctggcttg acccgcccac acggaggcct ccccagcgtt ttcttttcc cgagaagagc     360
tccagctcgc aggtccttag aacacggcag agcaggagca tctcaggaac caacggccag    420
ctccttggcg ctgtccccag ccccacaggc ctgctgcggc catccgcaaa cgggcatttc    480
cttgaacttt tgagagtgcc tttgaccagc tgttcgcagc tgggaaactc caacttttga    540
agtcagagct tggagcggcc cccgcaaggg cgtggctcaa accctcccca gagctgggag    600
ccattgctta tgcaagcccg tttcttttga tgtaaagatg gaagtcgtta ctatatttta    660
ataatgcaaa tacatctttt aaaataagtt aacatttctt accaccagat ggatcaggct    720
ttgaatttaa tcatgtaaat gtttgtaatt ttatgtcatt ttgttaaaat gggacgcttt    780
caattggttt ccaagaaaga tgatacctct gcattttctg gtggaaaagg tgtaataccc    840
ttaatgagat caaagtgtta ggggaaaaaa attccaaaag tagttacaag ctatatcaat    900
gtcaaagtaa atgcacttca tcaaagctaa gaagtcacag gaattgttct caggttttta    960
aaaaaatttt tcctgaattc aggaagtgtc ttctgaatag cagctagcca aataaagcgg    1020
tgtgtgtgta ctgcagctgt aggtgaactt aaaaataata ataaaagaa caaataaagc    1080
agtgtgtacc agccaaaaaa aaaaaaaa                                       1108

<210> SEQ ID NO 9
<211> LENGTH: 1290
<212> TYPE: DNA
<213> ORGANISM: Homo sapiens
<220> FEATURE: -
<223> OTHER INFORMATION: 1867351CB1

<400> SEQUENCE: 9
tctctagctc ctgggagagt gctccctgga gcacccaagc cagcgctggt gggatcatcg     60
gtgttcgtga aggagtgagt ggaggggcac tctgcgataa gatttctttt atttattcac    120
tgtagcaata gtgtcctgaa ttaactttct ctccactatt agcacatatt cctttttatac   180
atagccctt ataaaatga aaaaaaaaaa tcccttttaa gctgctaagt tccttttcc       240
tcccagggtg ccctgaaaac cttgaaggaa ttttaacgaa cgatgttgga agacaggcg     300
agcctcagtc agatcagcag atgcgccaag aagaaccttt gccggaacat ccacaggacg    360
gcgctaaatt gtccaggaaa cagctggtgc tgcggcgagg gcttctgctc ctgggggtct    420
tcttaatctt gctggtgggg attttagtga gattctatgt cagaattcag tgacgtggta    480
ggaaagaaag tcaggtcaag tgatgctttt gagcttacac acaattcaca ggcccaccag    540
tgacaattta ctgtgagtta atgtcattca ggtgtgccca tggattttga gggctggaaa    600
tgcaaagaca cattttttcta taaaagaaa aagcaactaa ggttaaaagc tatattgtgg    660
cccaagacac tgtctgaaag atgacatgag tagtaattca ccactatctg aaccaagcaa    720
ggatcaatgt gctgactgca ttggccaatg gctttgatac ttctgctatt tttttagaca    780
caaacccata aactaactgc ttaagaattc atactgcttg aattatgtaa aatatatttt    840
acagtatatc tttccttggg ccttagatta ctattcactg ggcaaatggt attgttttt    900
ttttttttt ttttttttaat agacggaagt cttgctctgt catgcaggct ggagtgcggt    960
ggtgcgatca tagctcactg cagcctcgaa ctcttgggct tcaagcaatc ctcctgtgtc   1020
agccaccaga gtagctgaga ctacaggggt atgccaccat gcccagctgg catttgttaa   1080
```

```
tcttcatttg aggtctagat ctaggcactg tggacactga aaaacagttg ggaaatcttt      1140
cgagctgtgg aaatccaaac aaagactgat aattcctggt aggggtgtgt gcgtgacgta      1200
ctgcagcctc aacctcctgg gctcaagtga tcctcccacc tcagcctcct gagtagctga      1260
gaccacaggc gtgtgcccac acgcctagct                                       1290
```

<210> SEQ ID NO 10
<211> LENGTH: 139
<212> TYPE: PRT
<213> ORGANISM: Homo sapiens
<220> FEATURE: -
<223> OTHER INFORMATION: 3481942CD1

<400> SEQUENCE: 10

Met His Trp Leu Arg Lys Val Gln Gly Leu Cys Thr Leu Trp Gly
 1               5                  10                  15

Thr Gln Met Ser Ser Arg Thr Leu Tyr Ile Asn Ser Arg Gln Leu
                20                  25                  30

Val Ser Leu Gln Trp Gly His Gln Glu Val Pro Ala Lys Phe Asn
                35                  40                  45

Phe Ala Ser Asp Val Leu Asp His Trp Ala Asp Met Glu Lys Ala
                50                  55                  60

Gly Lys Arg Leu Pro Ser Pro Ala Leu Trp Trp Val Asn Gly Lys
                65                  70                  75

Gly Lys Glu Leu Met Trp Asn Phe Arg Glu Leu Ser Glu Asn Ser
                80                  85                  90

Gln Gln Ala Ala Asn Val Leu Ser Gly Ala Cys Gly Leu Gln Arg
                95                 100                 105

Gly Asp Arg Val Ala Val Leu Pro Arg Val Pro Glu Trp Trp
               110                 115                 120

Leu Val Ile Leu Gly Cys Ile Arg Ala Gly Leu Ile Phe Met Pro
               125                 130                 135

Gly Thr Ile Arg

<210> SEQ ID NO 11
<211> LENGTH: 89
<212> TYPE: PRT
<213> ORGANISM: Homo sapiens
<220> FEATURE: -
<223> OTHER INFORMATION: 1900433CD1

<400> SEQUENCE: 11

Met Glu Arg Val Thr Leu Ala Leu Leu Leu Ala Gly Leu Thr
 1               5                  10                  15

Ala Leu Glu Ala Asn Asp Pro Phe Ala Asn Lys Asp Pro Phe
                20                  25                  30

Tyr Tyr Asp Trp Lys Asn Leu Gln Leu Ser Gly Leu Ile Cys Gly
                35                  40                  45

Gly Leu Leu Ala Ile Ala Gly Ile Ala Ala Val Leu Ser Gly Lys
                50                  55                  60

Cys Lys Tyr Lys Ser Ser Gln Lys Gln His Ser Pro Val Pro Glu
                65                  70                  75

Lys Ala Ile Pro Leu Ile Thr Pro Gly Ser Ala Thr Thr Cys
                80                  85

<210> SEQ ID NO 12
<211> LENGTH: 285

```
<212> TYPE: PRT
<213> ORGANISM: Homo sapiens
<220> FEATURE: -
<223> OTHER INFORMATION: 2673009CD1

<400> SEQUENCE: 12
```

Met Lys Val Thr Val Gly Pro Asp Pro Ser Leu Val Tyr Arg Pro
 1               5                  10                  15

Asp Val Asp Pro Glu Val Ala Lys Asp Lys Ala Ser Phe Arg Asn
                 20                  25                  30

Tyr Thr Ser Gly Pro Leu Leu Asp Arg Val Phe Thr Thr Tyr Lys
                 35                  40                  45

Leu Met His Thr His Gln Thr Val Asp Phe Val Arg Ser Lys His
                 50                  55                  60

Ala Gln Phe Gly Gly Phe Ser Tyr Lys Lys Met Thr Val Met Glu
                 65                  70                  75

Ala Val Asp Leu Leu Asp Gly Leu Val Asp Glu Ser Asp Pro Asp
                 80                  85                  90

Val Asp Phe Pro Asn Ser Phe His Ala Phe Gln Thr Ala Glu Gly
                 95                 100                 105

Ile Arg Lys Ala His Pro Asp Lys Asp Trp Phe His Leu Val Gly
                110                 115                 120

Leu Leu His Asp Leu Gly Lys Val Leu Ala Leu Phe Gly Glu Pro
                125                 130                 135

Gln Trp Ala Val Val Gly Asp Thr Phe Pro Val Gly Cys Arg Pro
                140                 145                 150

Gln Ala Ser Val Val Phe Cys Asp Ser Thr Phe Gln Asp Asn Pro
                155                 160                 165

Asp Leu Gln Asp Pro Arg Tyr Ser Thr Glu Leu Gly Met Tyr Gln
                170                 175                 180

Pro His Cys Gly Leu Asp Arg Val Leu Met Ser Trp Gly His Asp
                185                 190                 195

Glu Tyr Met Tyr Gln Val Met Lys Phe Asn Lys Phe Ser Leu Pro
                200                 205                 210

Pro Glu Ala Phe Tyr Met Ile Arg Phe His Ser Phe Tyr Pro Trp
                215                 220                 225

His Thr Gly Arg Asp Tyr Gln Gln Leu Cys Ser Gln Gln Asp Leu
                230                 235                 240

Ala Met Leu Pro Trp Val Arg Glu Phe Asn Lys Phe Asp Leu Tyr
                245                 250                 255

Thr Lys Cys Pro Asp Leu Pro Asp Val Asp Lys Leu Arg Pro Tyr
                260                 265                 270

Tyr Gln Gly Leu Ile Asp Lys Tyr Cys Pro Gly Ile Leu Ser Trp
                275                 280                 285